United States Patent

Korotko et al.

[11] Patent Number: 5,312,405
[45] Date of Patent: May 17, 1994

[54] SPINAL ROD COUPLER

[75] Inventors: Joseph R. Korotko, Fort Wayne; Randall N. Allard, Plymouth, both of Ind.

[73] Assignee: Zimmer, Inc., Warsaw, Ind.

[21] Appl. No.: 909,509

[22] Filed: Jul. 6, 1992

[51] Int. Cl.⁵ ............................................. A61B 17/56
[52] U.S. Cl. ................................................ 606/61; 606/72
[58] Field of Search ................................... 606/53–59, 606/61, 62, 72, 73

[56] References Cited

U.S. PATENT DOCUMENTS

| | | | |
|---|---|---|---|
| 4,269,178 | 5/1981 | Keene | 606/61 |
| 4,433,677 | 2/1984 | Ulrich | 606/61 |
| 4,805,602 | 2/1989 | Puno | 606/61 |
| 4,815,453 | 3/1989 | Cotrel | 606/61 |
| 4,946,458 | 8/1990 | Harms et al. | 606/61 |
| 4,957,495 | 9/1990 | Kluger | 606/61 |
| 5,005,562 | 4/1991 | Cotrel | 606/61 |
| 5,010,879 | 4/1991 | Moriya | 606/61 |
| 5,084,048 | 1/1992 | Jacob et al. | 606/61 |
| 5,102,412 | 4/1992 | Rogozinski | 606/61 |
| 5,129,388 | 7/1992 | Vignaud | 606/61 |
| 5,129,899 | 7/1992 | Small | 606/61 |
| 5,154,718 | 10/1992 | Cozad | 606/61 |

FOREIGN PATENT DOCUMENTS

0441729A1 2/1991 European Pat. Off. .

Primary Examiner—Michael A. Brown
Attorney, Agent, or Firm—Todd A. Dawson

[57] ABSTRACT

The coupler of this invention includes a two-piece coupler for a spinal rod including a yoke and a coupler body which may be positioned to clamp onto the spinal rod at an angle other than perpendicular relative to the rod. The yoke and body permit the spinal rod to be positioned plus or minus 15 degrees out of true perpendicular relative to the rod without sacrificing clamping strength. This advantage is particularly useful when the couplers are connected to a rod-to-rod interconnecting device to permit the rods to be less than parallel relative to one another. The accommodation of less than parallel rods or the non-perpendicular connection of device to the spinal rods reduces the non-functional exact positioning of the spinal rods during surgery as is required by current couplers. Further, the coupler can be placed from a superior position requiring minimal space without the need for screws to provide fixation to the rod.

2 Claims, 3 Drawing Sheets

SPINAL ROD COUPLER

FIELD OF THE INVENTION

This invention relates to couplers for spinal rods and has specific relevance to a coupler having a body and a yoke for clamping connection to a spinal rod wherein the coupler body and yoke may be less than non-perpendicular with the spinal rod.

BACKGROUND OF THE INVENTION

Heretofore, couplers for connecting devices such as an open back hook or screw require the device to be substantially perpendicular to the supporting spinal rod. Such a requirement calls for the surgeon to position a spinal rod in an exact position for proper connection. If the coupler is part of a rod to rod coupler, the spinal rods must be parallel to one another at their connection. This requirement for such an exacting rod position may lead to additional surgery time and may add further complications to an already complex and lengthy procedure to correct a spinal problem.

SUMMARY OF THE INVENTION

The coupler of this invention eliminates the problems discussed above by providing a two-piece coupler for a spinal rod including a yoke and a coupler body which may be positioned to clamp onto the spinal rod at an angle other than perpendicular relative to the rod. The yoke and body permit the spinal rod to be positioned plus or minus 15 degrees out of true perpendicular relative to the rod without sacrificing clamping strength. This advantage is particularly useful when the couplers are connected to a rod to rod interconnecting device to permit the rods to be less than parallel relative to one another. The accommodation of less than parallel rods or the non-perpendicular connection of the device to the spinal rods reduces the non-functional exact positioning of the spinal rods during surgery as is required by current couplers.

Accordingly, it is an object of the invention to provide for a novel coupler for a spinal rod.

Another object of the invention is to provide for a coupler for a spinal rod which accommodates a non-perpendicular connection between the rod and coupler.

Another object of the invention is to provide for a two-piece coupler for a spinal rod having a yoke and a body which may be positioned with the center axes out of alignment.

Still other objects of the invention will become apparent upon a reading of the following description taken with the accompanying drawings.

DESCRIPTION OF THE PREFERRED EMBODIMENTS

The preferred embodiments herein described are not intended to be exhaustive or to limit the invention to the precise forms disclosed. Rather, they are chosen and described to best explain the invention so that others skilled in the art might utilize their teachings.

Referring now to FIGS. 1, 2, and 4–6, the coupler of the invention is illustrated in conjunction with a telescopic rod to rod coupler 10. It should be understood that the invention described here is the coupler which includes a yoke and body. The body may be connected or formed to include a number of useful devices for spinal surgery such as a screw, a hook, or as illustrated in FIGS. 1, 2, and 4–6, a rod to rod coupler.

Figure 7:
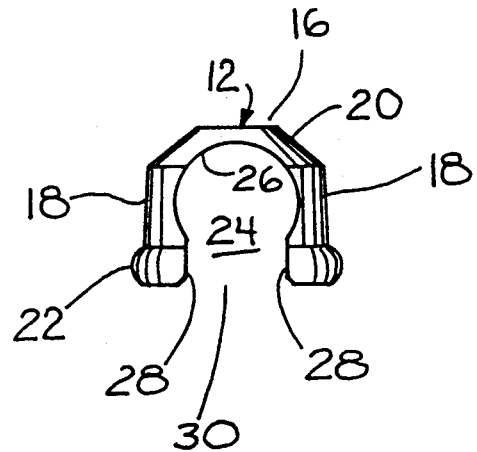
FIG. 7 is a plan view of the yoke.

Coupler 10 of the invention, as illustrated in FIGS. 1, 2, and 4–6, includes a generally inverted U-shaped yoke 12 and a body 14. The U-shaped yoke 12 defines an upper wall 16 having a pair of integral legs 18 extending downwardly therefrom having an arcuate outer periphery. The upper wall 16 includes an external beveled edge 20. The distal end of each leg 18 includes a lip 22 extending outwardly and generally perpendicular from the lower edges thereof. As illustrated in the figures, lip 22 extending from each leg 18 is arcuate following the arcuate periphery of the attached leg. As best illustrated in FIG. 7, the internal opening 24 of the yoke includes a generally arcuate portion 26 bordered on two sides by flat portions 28. As illustrated in FIG. 7, the aperture 30 formed between flat portions 28 is slightly narrower than the aperture formed by arcuate portion 26. Body 14 is generally C-shaped and includes an opening 32 for accommodating yoke 12. A centered and beveled recess 34 is formed in body 14 in communication with opening 32. Recess 34 forms a slight lip 36 on each end of the opening. Lips 36 constitute an abutment to prevent the yoke from shifting out of the opening in a direction parallel to the axis of the opening. A pair of slots 38 are formed in body 14 in communication with opening 32 near the open end of C-shaped body 14 as illustrated in the figures. Bodies 14 of the rod to rod coupler of FIGS. 1, 2, and 4–6 includes mutually cooperating rod portions 40 which telescopically engage one another to adjust the spacing between coupler bodies 14. A clamp 42 is provided on one rod portion 40 to fix the rod portions 40 relative to one another.

Figure 1:
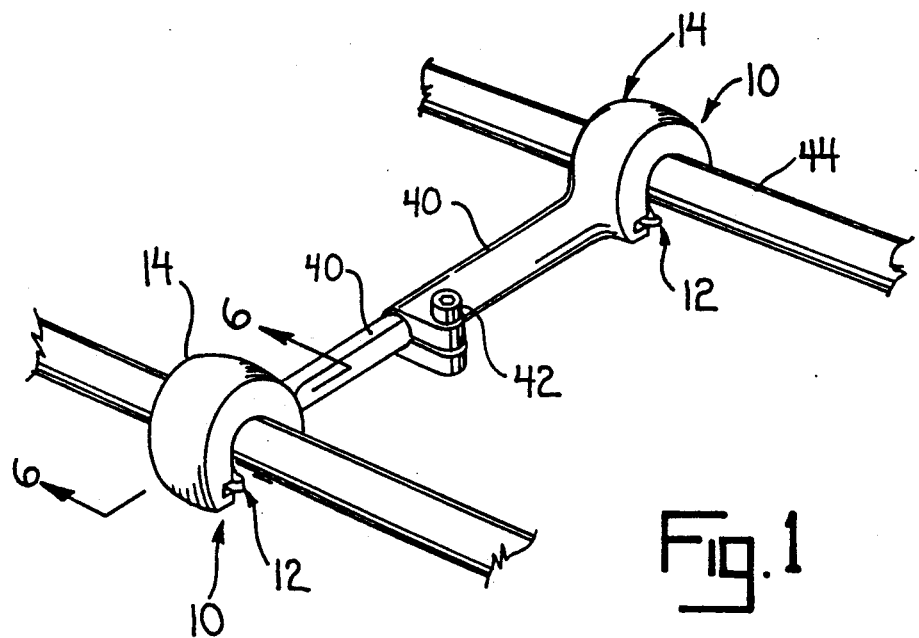
FIG. 1 is a perspective view of the coupler of the invention shown in use in association with a rod to rod coupler.
Figure 2:
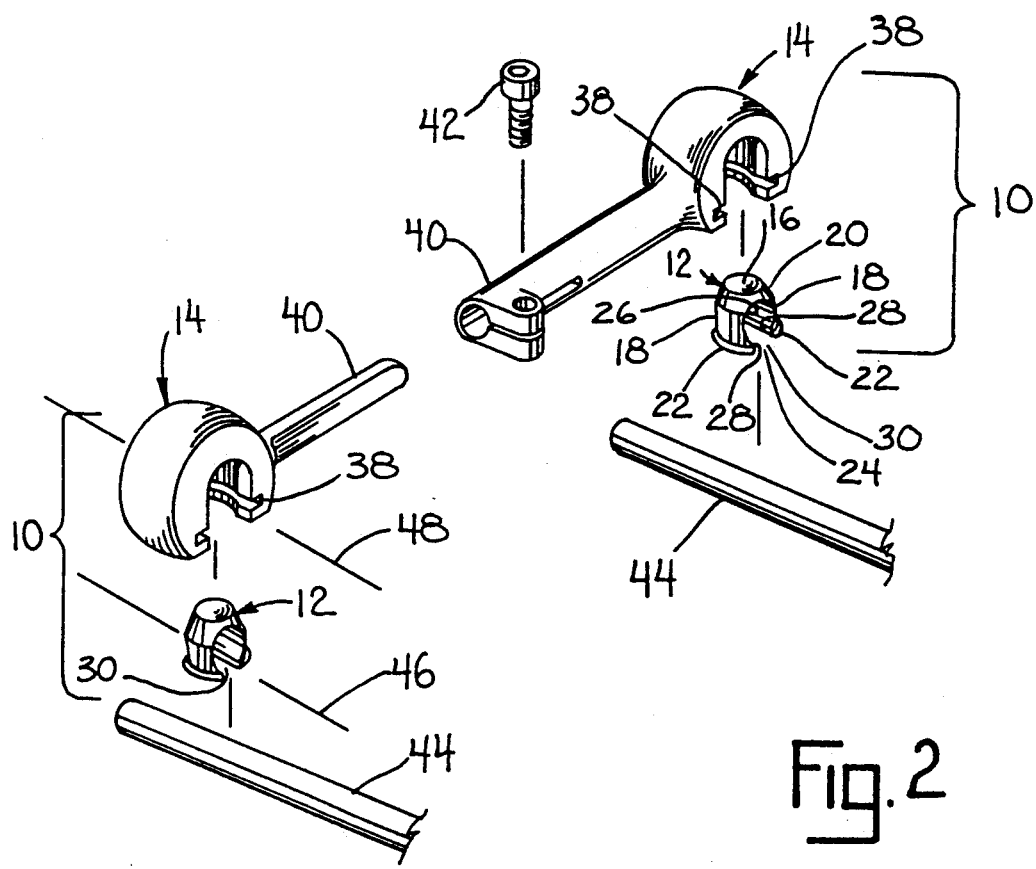
FIG. 2 is an exploded view of FIG. 1.
Figure 4:
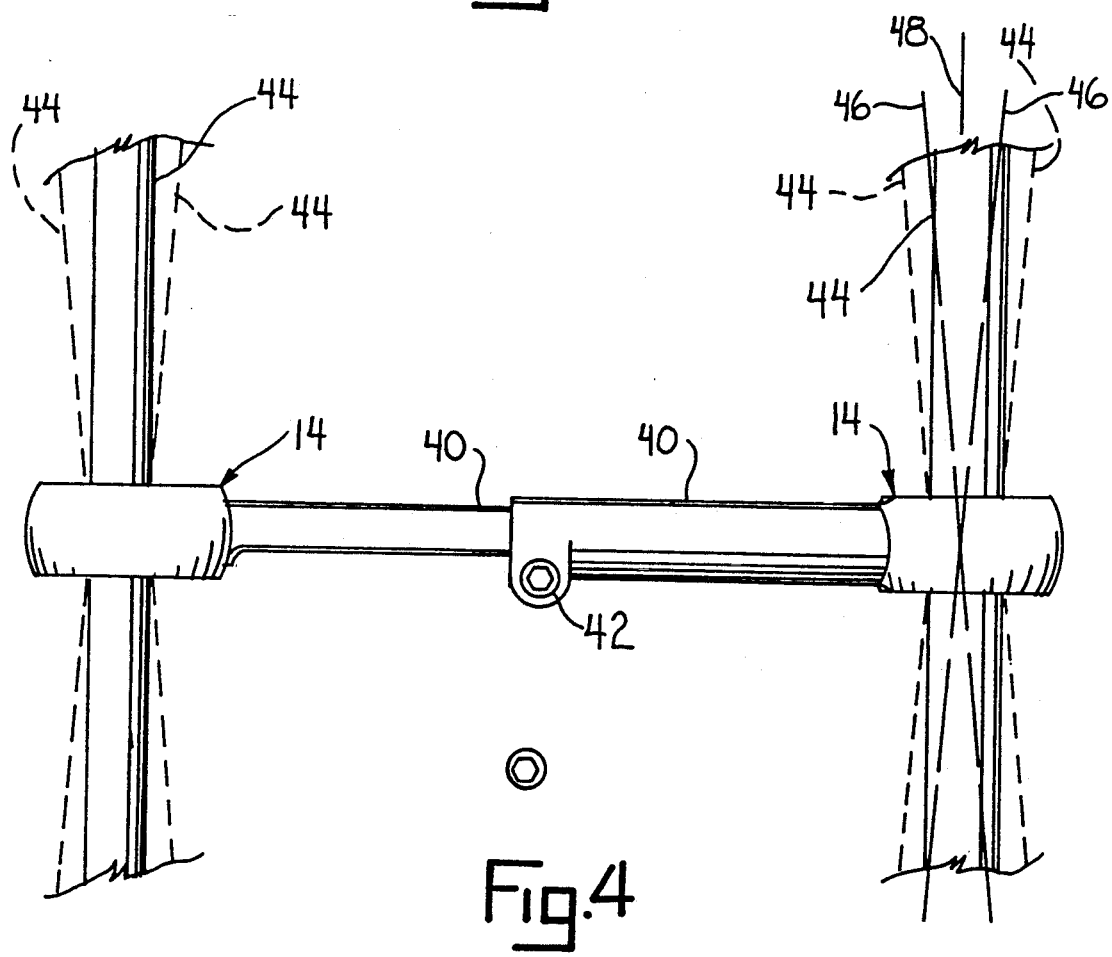
FIG. 4 is a plan view of FIG. 1 illustrating in broken lines the range of motion of spinal rods relative to the coupler.
Figure 5:
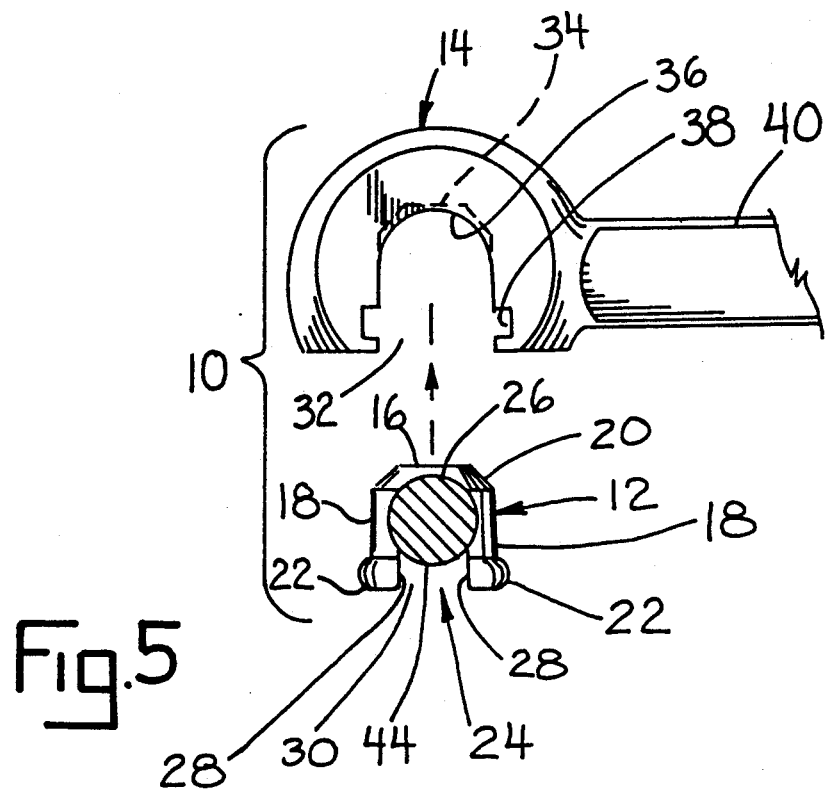
FIG. 5 is a plan view with the spinal rod sectioned illustrating the yoke positioned on the rod prior to the body being clamped onto the rod.
Figure 6:
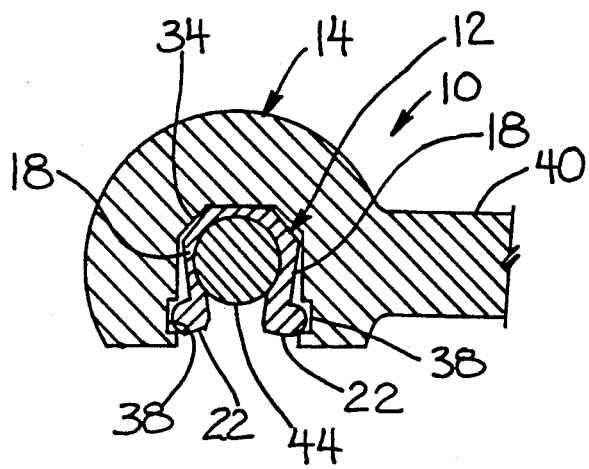
FIG. 6 is the view of FIG. 5 sectioned with the coupler body pressed onto the yoke and the yoke in clamping engagement with the rod.

In use, to secure two space spinal rod 44 to one another using the coupler of the invention, the surgeon would first place a yoke 12 onto each rod by snapping the yoke over the rod or by partially assembling the yoke and coupler then snapping the assembly on to the rod. The reduced opening between the flat portions 28 causes an interference between the rod and yoke. It should be understood that the diameter of the spinal rod is equal to or slightly larger than the diameter of the arcuate section 26 and aperature 30 of the yoke. Therefore, to snap the yoke onto the spinal rod, legs 18 yield slightly under force of the spinal rod to seat the rod within the arcuate section of the yoke. Once the yoke is seated, the surgeon places the C-shaped body on top of the yoke and using a compressing tool forces the body over the yoke until lips 22 of the yoke seat within slots 38 of the body. (See FIGS. 5 and 6). This orientation compresses legs 18 about the spinal rod to secure the rod, yoke and body together in fixed relationship. During assembly, after the yoke is placed onto the spinal rod, the axis 46 of the yoke opening is substantially parallel to the spinal rod with only a limited amount of axial movement. However, since lips 22 are arcuate, following the arcuate periphery of legs 18, the yoke may be positioned in clamping engagement about the spinal rod such that the axis of body opening 32, as defined by line 46 in FIG. 2, and the axis of yoke opening 24, as defined by line 48 in FIG. 2, are at a relative angle or otherwise non-parallel. The resulting connection between the spinal rod and the body 14 of the coupler is non-perpendicular. FIG. 4 illustrates the range of variance able to be achieved with the coupler of the invention. It should be understood that the yoke axis 46 is parallel to the longitudinal axis of the rod; therefore the resultant angle between the rod and body 14 reflects the relative angle between the yoke and body. Contact between the spinal rod 44 and the edges of the C-shaped body about opening 32 define the angular extremes at which the spinal rod may be positioned. It should be explicitly understood that the range of angles or extreme positions possible using the invention as illustrated in FIG. 4 is only possible prior to the body 14 being compressed onto the yoke 14. Once the spinal rod, yoke, and body are compressed into the assembly of FIG. 6, the assembly is rigidly fixed to one another and does not permit movement.

Figure 3:
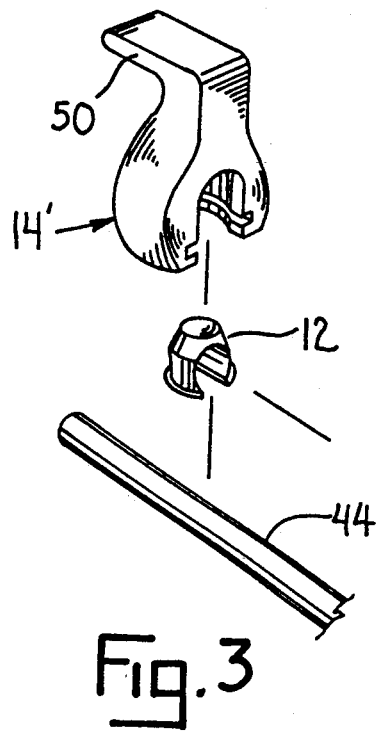
FIG. 3 is an exploded view of the coupler in association with a spinal rod and a spinal hook.

The embodiment of FIG. 3 is provided as an illustrative example of the coupler mechanism of the invention used in conjunction with a spinal hook. In the illustration of FIG. 3, the spinal rod 44 and yoke 12 are identical in form and function to elements described above. The body 14' is operatively identical to body 14 previously described so far as the interworkings with the yoke and spinal rod are concerned. The difference between bodies 14 and 14' is that body 14' includes a hook 50 extending from the body as opposed to the rod portion 40 described earlier. In the embodiment of FIG. 3 the hook 50 would be for connection of a spinal rod to a vertebra of the patient.

The examples of possible use of the coupler mechanism of the invention should not be considered a limitation but are provided merely to more fully illustrate the usefulness of the invention. The coupler mechanism of the invention may find application in any number of situations not illustrated here such as, for example, in conjunction with a spinal screw.

Finally, it should be understood that the invention should not be limited to the details above but may be amended within the scope of the appended claims.

We claim:

1. A coupler for connection to a spinal rod, said coupler comprising a yoke means including an opening for accommodating the spinal rod, the opening of the yoke means defining an axis a body means including an opening for accommodating the yoke means in compressing engagement with the spinal rod, the opening of the body defining an axis, wherein the body means accommodates the yoke means such that the axis of the opening of the yoke means is non-parallel to the axis of the body means, said yoke means includes a generally U-shaped body having a pair of integral legs, each of the legs including a lip extending outwardly therefrom generally transverse to the legs, the body means being generally C-shaped and including a pair of slots in communication with the opening of said body means, each slot accommodating a lip of the yoke means in an interference fit to retain the yoke means within the opening of the body means.

2. The coupler of claim 1 wherein the body means further includes at least one lip extending over the opening of the body means to constitute a stop member to prevent the yoke means from shifting laterally relative to the opening of the body means.

* * * * *